United States Patent [19]
Whalen et al.

[11] Patent Number: 5,573,523
[45] Date of Patent: Nov. 12, 1996

[54] FLUSHABLE SANITARY MINI-PAD

[76] Inventors: Johanna B. Whalen, 5904 Jaybird Cir., Davenport, Iowa 52807; Trudy Battaille, Tembroek 1, B-1540 Herne, Belgium

[21] Appl. No.: 386,030

[22] Filed: Feb. 9, 1995

[51] Int. Cl.⁶ .................................................. A61F 13/15
[52] U.S. Cl. ...................... 604/374; 604/358; 604/367; 156/288; 156/305
[58] Field of Search ........................... 604/364, 374, 604/367, 358; 156/288, 305

[56] References Cited

U.S. PATENT DOCUMENTS

| | | |
|---|---|---|
| 1,564,498 | 3/1925 | Thomas . |
| 1,702,530 | 2/1929 | Williams . |
| 1,850,033 | 3/1932 | Ritter . |
| 2,408,508 | 12/1942 | Canavan . |
| 2,771,882 | 9/1952 | Leupold . |
| 2,917,049 | 12/1959 | Delaney . |
| 3,420,235 | 7/1966 | Harmon . |
| 3,480,046 | 11/1969 | Costanza . |
| 3,575,173 | 4/1971 | Loyer . |
| 3,804,092 | 4/1974 | Tunc ...................................... 128/284 |
| 3,939,836 | 2/1976 | Tunc ...................................... 128/284 |
| 3,983,373 | 10/1976 | Hirschman . |
| 4,595,392 | 6/1986 | Johnson et al. . |
| 4,627,848 | 12/1986 | Lassen et al. . |
| 4,631,062 | 12/1986 | Lassen et al. . |
| 4,743,245 | 5/1988 | Lassen et al. . |
| 4,944,734 | 7/1990 | Wallach ................................ 604/358 |
| 5,160,331 | 11/1992 | Forester et al. ...................... 604/364 |
| 5,185,009 | 2/1993 | Sitnam ................................. 604/364 |
| 5,207,662 | 5/1993 | James .................................. 604/364 |
| 5,300,358 | 4/1994 | Evers ................................... 604/364 |

FOREIGN PATENT DOCUMENTS 2034605  7/1992  Canada ............................... 604/385.2

Primary Examiner—John G. Weiss
Assistant Examiner—Dennis Ruhl
Attorney, Agent, or Firm—Henderson & Sturm

[57] ABSTRACT

A totally biodegradable and therefore flushable, mini-pad with a unique kite shape which minimizes movement or slippage. A filler of cellulose fragments is sandwiched between cellulose panels which are then sealed about their circumference by heat and pressure. The kite shaped pad has a length of approximately fourteen centimeters and a width of approximately ten centimeters, and therefore fits comfortably and securely between the thighs while providing adequate coverage of the labia.

9 Claims, 1 Drawing Sheet

Fig. 1
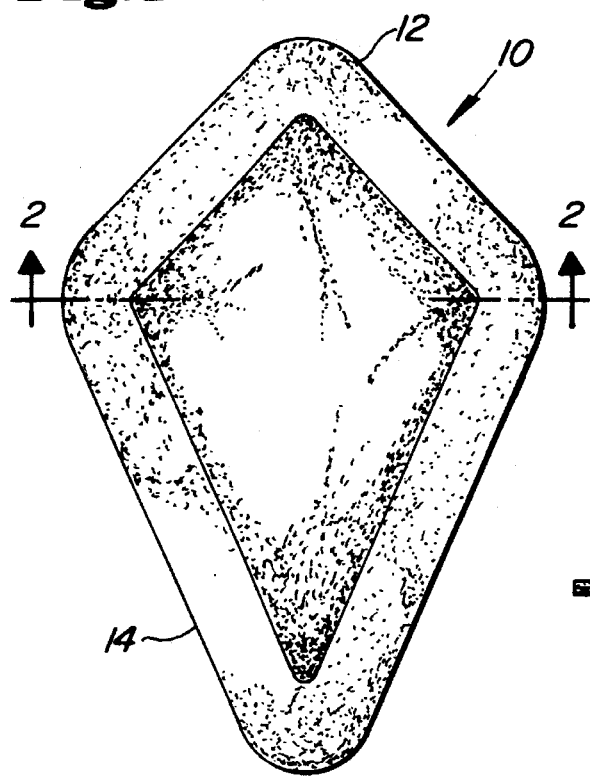
Fig. 2
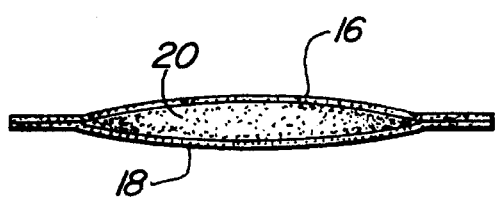
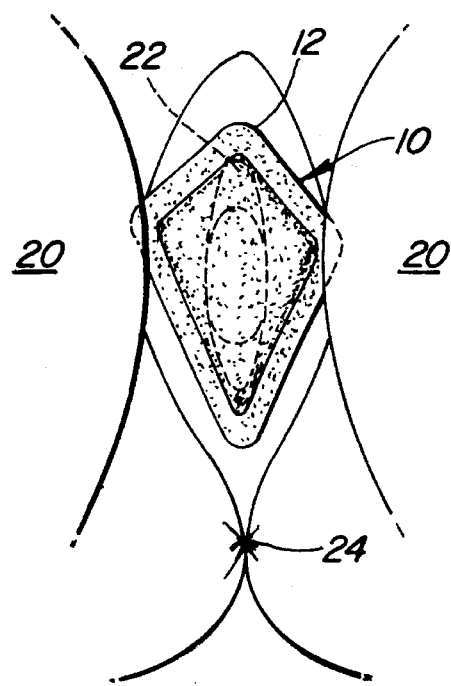
Fig. 3

FLUSHABLE SANITARY MINI-PAD

TECHNICAL FIELD

This invention relates to sanitary appliances for personal feminine care, and more particularly to a mini-pad which may be safely disposed of by flushing it into the sewer system and which is shaped to prevent shifting of the device during wear without the use of adhesives or belts.

BACKGROUND ART

The prior art is replete with all manner and variety of devices for the absorption of bodily fluids such as those from monthly menstrual flow, vaginal discharge and minor urinary incontinence. These externally worn devices generally fall into two broad categories: sanitary napkins and mini-pads or panty liners. Sanitary napkins, being larger and therefore capable of greater absorption, are worn during periods of heavy menstrual flow. Mini-pads are worn when menstrual flow has decreased and for daily use to absorb small volumes of vaginal discharge or urine leakage.

Typical sanitary napkins and mini-pads are constructed from multiple layers of fluid absorbent material with a fluid impermeable backing and a fluid permeable facing. The backing is often coated with a mild adhesive to hold the device in position within the undergarment.

DISCLOSURE OF THE INVENTION

The present invention discloses a totally biodegradable, and therefore flushable, mini-pad with a unique kite shape which minimizes movement or slippage. A filler of cellulose fragments is sandwiched between cellulose panels which are then sealed about their circumference by heat and pressure. The pad has a length of approximately fourteen centimeters and a width of approximately ten centimeters, and therefore fits comfortably and securely between the thighs while providing adequate coverage of the labia.

BRIEF DESCRIPTION OF THE DRAWINGS

These and other attributes of the invention will become more clear upon a thorough study of the following description of the best mode for carrying out the invention, particularly when reviewed in conjunction with the drawings, wherein:

FIG. 1 is a plan view of the invention;

FIG. 2 is a sectional view taken along line 2—2 of FIG. 1; and

FIG. 3 depicts the proper placement of the device.

BEST MODE FOR CARRYING OUT THE INVENTION

Referring now to the drawings, wherein like reference numerals designate identical or corresponding parts throughout the several views, FIG. 1 is a plan view of the invention 10 which, in a preferred embodiment, has a kite shape with the short axis having a length of approximately seven to thirteen centimeters and the long axis having a length of approximately ten to seventeen centimeters. The shorter end of the kite shape is the anterior end 12, while the longer end is the posterior end 14. Referring also to FIG. 2, it can be seen that the pad is comprised of an upper panel 16 fabricated from a cellulose material having properties similar to tissue paper or made of tissue paper, a thicker lower panel 18 of like material, and a central core 20 of cellulose particles or fibers having a thickness of approximately one centimeter. Preferably, the panels 16, 18 are biodegradable. The fluid absorbent filler may be fabricated from shredded tissue paper. The two panels 16, 18 are bonded together about their circumference by mechanical means, preferably by wetting the opposed edges and then heating under pressure. This avoids the use of any adhesives and therefore enhances the biodegradation of the pad.

Placement of the pad 10 is depicted in FIG. 3 where it is placed between the thighs 20 with the anterior end 12 lying anterior to the clitoral region 22 and the posterior end lying just in front of the anus 24. Lateral movement is prevented by the thighs, with the undergarment providing sufficient pressure to ensure minimal slippage.

Those skilled in the art will recognize that many modifications and variations of the present invention are possible in light of the above teachings. For example, many different shapes and sizes of the invention are available, although the kite shape disclosed is believed to be the preferred embodiment. It is therefore to be understood that, within the scope of the appended claims, the invention may be practiced otherwise than as specifically described.

What is claimed is:

1. A totally biodegradable sanitary pad which may be safely disposed of into a sewage system, comprising:

(a) a first panel of biodegradable material, fabricated from tissue paper; and (b) a second panel of biodegradable material, fabricated from tissue paper; and (c) a fluid-absorbent biodegradable filler fabricated from shredded tissue paper sandwiched between said first panel and said second panel, said first panel and said second panel being mechanically bonded about their circumference.

2. The biodegradable sanitary pad of claim 1 wherein said first panel and said second panel are substantially kite shaped.

3. The biodegradable sanitary pad of claim 2 wherein said first panel and said second panel have a short axis length of approximately seven to thirteen centimeters and a long axis length of approximately ten to seventeen centimeters.

4. A totally biodegradable sanitary pad which may be safely disposed of into a sewage system, consisting of:

(a) a first panel of biodegradable material, fabricated from tissue paper; and (b) a second panel of biodegradable material, fabricated from tissue paper; and (c) a fluid-absorbent biodegradable filler fabricated from shredded tissue paper sandwiched between said first panel and said second panel, said first panel and said second panel being mechanically bonded about their circumference.

5. The biodegradable sanitary pad of claim 4 wherein said first panel and said second panel are substantially kite shaped.

6. The biodegradable sanitary pad of claim 5 wherein said first panel and said second panel have a short axis length of approximately seven to thirteen centimeters and a long axis length of approximately ten to seventeen centimeters.

7. A method of creating a totally biodegradable sanitary pad comprising the steps of:

(a) sandwiching a biodegradable, fluid-absorbent filler fabricated from shredded tissue paper between a first biodegradable panel and a second biodegradable panel, said panels having fabricated from tissue paper; and (b) mechanically bonding said first biodegradable panel and said second biodegradable panel around their circumference.

8. The method as recited in claim 7 wherein said mechanical bonding step further comprises the steps of wetting edges of said first biodegradable panel and said second biodegradable panel and then applying heat and pressure thereto.

9. The method as recited in claim 8 wherein said first biodegradable panel and said second biodegradable panel are substantially kite shaped.

\* \* \* \* \*